United States Patent [19]
Minamizono et al.

[11] 4,322,494
[45] Mar. 30, 1982

[54] PHOTOGRAPHIC LIGHT-SENSITIVE MATERIAL

[75] Inventors: Junji Minamizono; Yoshiro Kawashima; Shingo Ishimaru; Noriyuki Inoue, all of Minami-ashigara, Japan

[73] Assignee: Fuji Photo Film Co., Ltd., Kanagawa, Japan

[21] Appl. No.: 227,907

[22] Filed: Jan. 23, 1981

[30] Foreign Application Priority Data

Jan. 23, 1980 [JP] Japan .................................. 55/6510

[51] Int. Cl.$^3$ .......................... G03C 1/28; G03C 1/34
[52] U.S. Cl. .................................... 430/599; 430/600; 430/603; 430/607; 430/613; 430/614
[58] Field of Search ............... 430/599, 600, 603, 607, 430/613, 614

[56] References Cited

U.S. PATENT DOCUMENTS

| | | | |
|---|---|---|---|
| 3,652,277 | 3/1972 | Hara et al. | 430/614 |
| 3,788,859 | 1/1974 | Nakazawa et al. | 430/607 |
| 3,843,368 | 10/1974 | Yamamoto et al. | 430/528 |
| 4,237,214 | 12/1980 | Mifune | 430/599 |

*Primary Examiner*—Won H. Louie, Jr.
*Attorney, Agent, or Firm*—Sughrue, Mion, Zinn, Macpeak & Seas

[57] ABSTRACT

A silver halide photographic light-sensitive material is described containing a compound comprising at least one unsaturated group and at least one betaine group in at least one layer thereof.

The photographic light-sensitive material has a high sensitivity without being accompanied by an undesirable increase in the formation of fog.

18 Claims, No Drawings

PHOTOGRAPHIC LIGHT-SENSITIVE MATERIAL

BACKGROUND OF THE INVENTION

The present invention relates to a photographic light-sensitive material and more particularly to a chemically sensitized silver halide photographic light-sensitive material.

Various means of chemical sensitization for increasing the light sensitivity of silver halide photographic emulsions are known. One typical method is known as sulfur sensitization, wherein the light sensitivity of a silver halide photographic emulsion is increased by adding thereto a very small amount of sulfur or a sulfur compound to form silver sulfide, as disclosed, for example, in U.S. Pat. Nos. 2,410,689 and 3,501,313, West German Pat. No. 1,422,869, and Japanese Pat. No. 20533/74.

Also, methods for increasing the light sensitivity of silver halide photographic emulsions by adding thereto a suitable reducing agent or gold compound, known as reduction sensitization and gold sensitization, respectively, are disclosed, for example, in U.S. Pat. Nos. 2,399,083 and 3,297,446.

Furthermore, it is known to increase the light sensitivity of silver halide emulsions by a combination of these sensitization methods, as described in T. H. James, *The Theory of the Photographic Process*, 4th Edition, pp. 149-160 (Macmillan Pub. Co., 1977).

In these conventional sensitization methods, as the amount of sensitizer is increased to obtain higher light sensitivity, the silver halide photographic emulsions tend to form fog, and it becomes difficult to control the formation of fog even by using antifoggants or stabilizers. Also, silver halide photographic emulsions sensitized by such conventional sensitization methods suffer from the disadvantage that when photographic films prepared by coating such silver halide emulsions are stored under high temperature and high humidity conditions, the photographic characteristics change greatly.

Attempts to improve the light sensitivity of silver halide emulsions by prolonging the chemical ripening period or increasing the ripening temperature are accompanied by an increase in the formation of fog, and it has been difficult to attain the desired purpose.

It is known to use a surface active agent having a betaine group as a coating aid for a photographic light-sensitive material, as described in U.S. Pat. No. 3,843,368. But such surface active agent does not have ability to increase the light sensitivity of silver halide emulsions.

SUMMARY OF THE INVENTION

It is, accordingly, a first object of the present invention to provide a photographic light-sensitive material, the sensitivity of which has been improved without being accompanied by an increase of fog harmful to the photographic characteristics.

A second object of the present invention is to provide a photographic light-sensitive material which is less subject to a reduction in sensitivity when stored under high temperature and high humidity conditions.

A third object of the present invention is to provide a method for increasing the sensitivity of a photographic light-sensitive material without an increase in fog harmful to the photographic characteristics.

These and other objects of the present invention, that will become more apparent from the following detailed description and Examples, are achieved by a silver halide photographic light-sensitive material comprising a support having coated thereon at least one silver halide emulsion layer, said photographic light-sensitive material containing a compound comprising at least one unsaturated group and at least one betaine group and having substantially no surface activity in at least one layer thereof.

DETAILED DESCRIPTION OF THE INVENTION

The above and other objects of the present invention can be attained by incorporating a compound, which is represented by the formula (I) hereinbelow and which has substantially no surface activity, into at least one of the constituent layers of the photographic light-sensitive material.

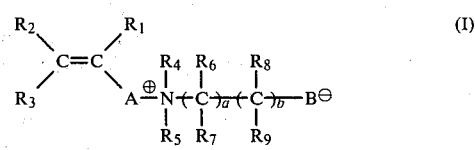

wherein $R_1$, $R_2$, and $R_3$, which may be the same or different, each represents hydrogen, an alkyl group (preferably having from 1 to 6 carbon atoms, and most preferably having from 1 to 4 carbon atoms), a carboxy group or a substituted alkyl group (preferably having from 1 to 6 carbon atoms, and most preferably having from 1 to 4 carbon atoms, with the substituent being a hydroxy group, a halogen atom, a nitro group, etc.); $R_4$ and $R_5$, which may be the same or different, each represents hydrogen, an alkyl group (preferably having from 1 to 6 carbon atoms, and most preferably having from 1 to 4 carbon atoms), a substituted alkyl group (preferably having from 1 to 6 carbon atoms, and most preferably having from 1 to 4 carbon atoms, with the substituent being a hydroxy group, a halogen atom, a nitro group, etc.) or an aralkyl group (preferably having from 7 to 11 carbon atoms), or $R_4$ and $R_5$ together represent an atomic group necessary to form a heterocyclic ring (for example, a morpholine ring, etc.), or $R_4$ or $R_5$ is bonding with A and represent an atomic group necessary to form a heterocyclic ring (for example, a pyridine ring, an imidazole ring, etc.) (the heterocyclic ring may be substituted, with the substituent preferably being an alkyl group, a hydroxy group, a halogen atom, a nitro group, etc.); $R_6$, $R_7$, $R_8$, and $R_9$, which may be the same or different, each represents hydrogen, an alkyl group (preferably having from 1 to 6 carbon atoms, and most preferably having from 1 to 4 carbon atoms) or a substituted alkyl group (the substituent being a hydroxy group, a halogen atom, a nitro group, etc.); A represents a divalent connecting group, and particularly preferably an ether group, an alkylene group (preferably having from 1 to 6 carbon atoms), a substituted alkylene group (preferably having from 1 to 6 carbon atoms, and the substituent being a hydroxy group, a halogen atom, a nitro group, etc.), an arylene group (preferably having from 6 to 11 carbon atoms), a substituted arylene group (preferably having from 6 to 11 carbon atoms, and the substituent being a hydroxy group, a halogen atom, a nitro group, etc.), an aralkylene group (preferably having from 8 to 12 carbon atoms), a substituted aralkylene group (preferably having from 8 to 12 carbon atoms, and the substituent being a hydroxy group, a halogen atom, a nitro group, etc.), a —COOR$_{10}$-group (wherein R$_{10}$ represents a divalent group, preferably an alkylene group, and particularly preferably an alkylene group having from 1 to 6 carbon atoms; an arylene group, and particularly preferably an arylene group having from 6 to 11 carbon atoms; an aralkylene group, and particularly preferably an aralkylene group having from 8 to 12 carbon atoms; or an atomic group forming a heterocyclic ring together with R$_4$ or R$_5$), a —OCO—R$_{10}$-group, a

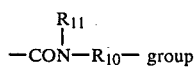
—CON—R$_{10}$— group (wherein R$_{11}$ represents hydrogen; an alkyl group, preferably an alkyl group having from 1 to 6 carbon atoms; or an atomic group forming in heterocyclic ring together with R$_4$ and R$_{10}$, or R$_5$ and R$_{10}$; or an atomic group forming a heterocyclic ring (for example, a pyridine ring, an imidazole ring, etc.) together with R$_4$ or R$_5$); a and b each represents 0 or a positive integer (preferably from 1 to 6, and particularly preferably from 1 to 4) provided that a and b are not both 0; and B represents —COO or —SO$_3$.

The compound of the formula (I) used in the present invention has substantially no surface activity. The "substantially no surface activity" means in the present invention that surface tension of 1 wt% aqueous solution of the compound is 45 dyne/cm or more.

Particularly preferred compounds are those represented by formula (I) wherein R$_1$, R$_2$, and R$_3$ each represents hydrogen, a lower alkyl group, or a carboxy group; R$_4$ and R$_5$ each represents a lower alkyl group, an atomic group forming a pyridine ring or an imidazole ring together with A, or R$_4$ and R$_5$ together represent an atomic group forming a morpholine ring; R$_6$, R$_7$, R$_8$, and R$_9$ each represents hydrogen or a methyl group; A represents

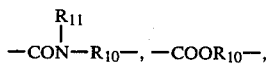
—CON—R$_{10}$—, —COOR$_{10}$—, or an atomic group forming a pyridine ring or an imidazole ring together with R$_4$ or R$_5$; and a and b each represents 0 or a positive integer from 1 to 4.

Of the betaine compounds represented by formula (I), representative examples of these compounds which are preferably used in the present invention are illustrated below, but the present invention is not to be construed as being limited thereto.

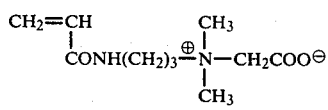
(1)

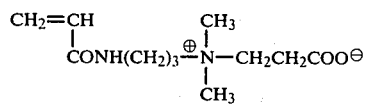
(2)

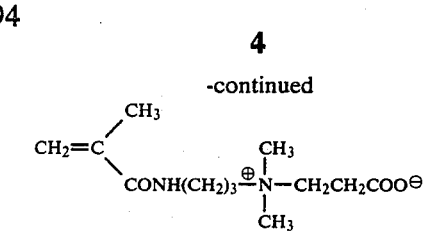
(3)

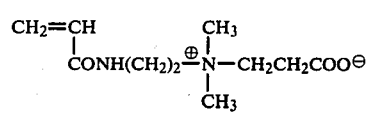
(4)

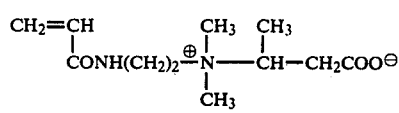
(5)

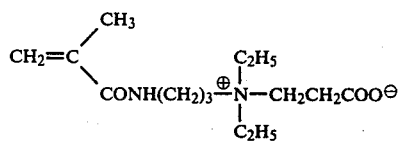
(6)

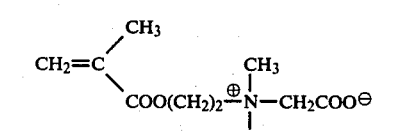
(7)

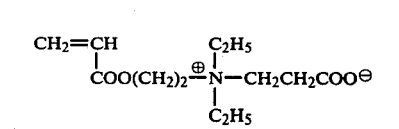
(8)

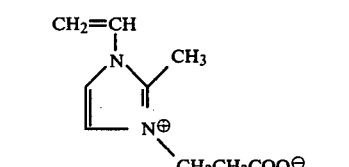
(9)

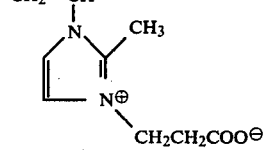

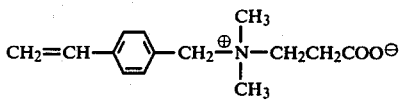
(10)

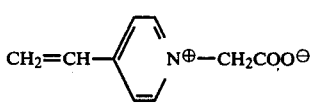
(11)

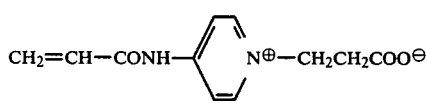
(12)

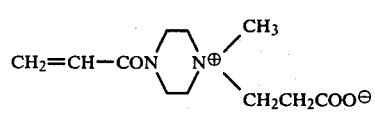
(13)

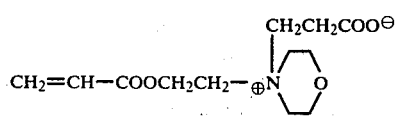
(14)

-continued

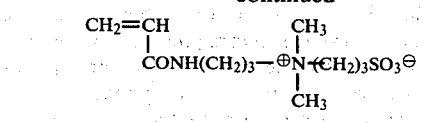 (15)

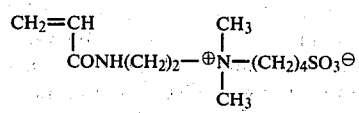 (16)

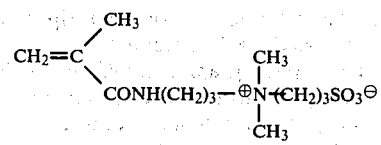 (17)

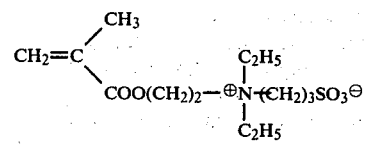 (18)

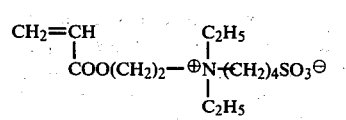 (19)

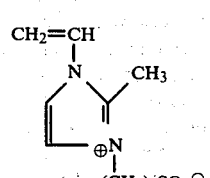 (20)

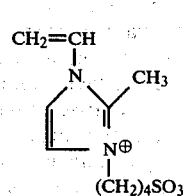 (21)

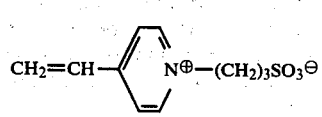 (22)

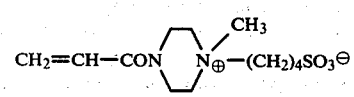 (23)

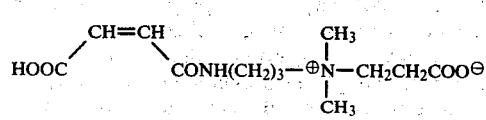 (24)

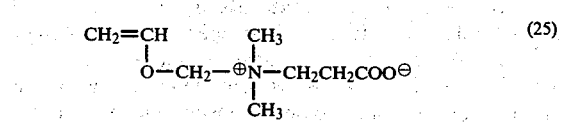 (25)

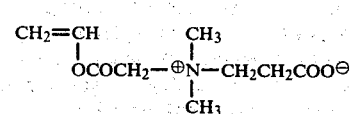 (26)

-continued

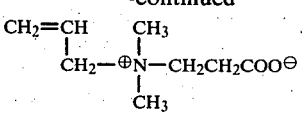 (27)

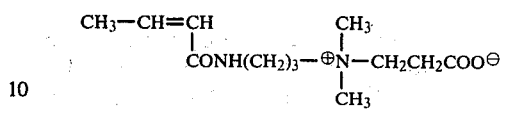 (28)

The compounds which can be used in the present invention can be synthesized with reference to the methods described, for example, in U.S. Pat. Nos. 2,777,872, 2,846,417, 3,411,912, 3,832,185, 4,012,437, Japanese Pat. Nos. 3832/70, 19951/70, 30293/71, 1040/74, and Polymer, Vol. 18, p. 1058 (1977), and so forth.

Synthesis examples of representative compounds which can be used in the present invention are illustrated below.

SYNTHESIS EXAMPLE 1

Synthesis of Compound (1)

94.5 g (1 mol) of monochloroacetic acid and 350 ml of methanol were put into a reaction vessel and stirred while maintaining a temperature of 0° to 5° C. 193 g of a 28% methanol solution of sodium methylate was gradually added dropwise thereto while maintaining a temperature of the system so as not to exceed 30° C. Then a solution mixture of 156.2 g (1 mol) of 3-acylamidopropyl dimethyl amine and 300 ml of methanol was added thereto (0.5 g of phenothiazine was added as a polymerization inhibitor). Then the mixture was heated so as to make the temperature of the system at 60° C. and stirred for 10 hours. The sodium chloride thus formed was removed by filtration, and the filtrate was crystallized in a large amount of acetone. The identification of the compound was carried out using NMR spectrum, elemental analysis, infrared absorption spectrum, etc. The yield of the reaction was 145 g (68%).

SYNTHESIS EXAMPLE 2

Synthesis of Compound (2)

72.06 g (1 mol) of β-propiolactone and 250 ml of acetonitrile were put into a reaction vessel and cooled the temperature of the system to −20° C. with stirring. A solution mixture of 170 g (1 mol) of 3-methacrylamidopropyl dimethyl amine and 700 ml of acetonitrile was added dropwise thereto while controlling the temperature of the system so as not to exceed −10° C. The reaction solution was allowed to stand overnight at from 0° C. to 5° C. while white hydroscopic crystals were deposited. The crystals were collected by filtration to obtain 202 g of Compound (2) (yield: 84%). The structure of the compound was confirmed by NMR spectrum, elemental analysis, and infrared absorption spectrum. The melting point of the compound was 109° C. to 111° C.

SYNTHESIS EXAMPLE 3

Synthesis of Compound (20)

70 g (0.58 mol) of 1,3-propanesultone and 800 ml of ethyl acetate were put into a reaction vessel and cooled to 10° C. with stirring. 50 g (0.46 mol) of 1-vinyl-2-methylimidazole was added dropwise thereto. The mixture was stirred for 1 hour at a temperature of 10° to 15° C. and the temperature was gradually elevated and stirred at 50° C. for 5 days. The crystals thus deposited were collected by filtration and dried to obtain 104 g of Compound (20) (yield 87%). The structure of the compound was confirmed by NMR spectrum, elemental analysis and infrared spectrum.

While the betaine compound according to the present invention can be added to any layer of the photographic light-sensitive material, it is preferably incorporated into a light-sensitive silver halide emulsion layer or a layer adjacent thereto.

When the betaine compound is incorporated into a silver halide emulsion layer, the betaine compound can be added at any stage of preparation of the emulsion, but it is preferred to add the compound during chemical ripening, or after chemical ripening but before coating of the emulsion.

The amount of the betaine compound used according to the present invention can be varied, depending upon the kind of silver halide emulsion, the kind of the compound used, etc., but it is preferably used in an amount of from about 0.001 to 1 mol, and preferably from 0.01 to 0.5 mol, per mol of silver halide.

The value of pAg (logarithm of the reciprocal of the silver ion concentration) during chemical ripening of the silver halide emulsion used in the present invention is preferably from about 8.0 to 11.0.

During chemical ripening, other chemical sensitizers may be added together with the compound of the present invention. Examples of such chemical sensitizers are the gold compounds described, for example, in U.S. Pat. Nos. 2,399,083, 2,597,856, 2,597,915, etc.; reducing materials as the amines, stannous salts, etc., described, for example, in U.S. Pat. Nos. 2,487,850, 2,518,698, etc.; the salts of noble metals as platinum, palladium, iridium, rhodium, etc.; and sulfur compounds as thioureas, thiazoles, rhodamines, etc., described, for example, in U.S. Pat. Nos. 2,410,698, 2,278,947, 2,728,668, 3,656,955, 4,032,928 and 4,067,740, West German Patent Application (OLS) No. 2,547,723, etc.

The silver halide used for the silver halide photographic emulsions of this invention includes silver bromide, silver iodobromide, silver chloroiodobromide, silver chlorobromide, and so forth.

The silver halide photographic emulsions of this invention may be prepared by the methods described in *Chimie et Physique Photographique*, edited by P. Glafkides (Paul Montel, 1967); G. F. Duffin, *Photographic Emulsion Chemistry* (The Focal Press, 1966); and V. L. Zelikman, et al., *Making and Coating Photographic Emulsion* (The Focal Press, 1964).

Also, a cadmium salt, a zinc salt, a lead salt, a thallium salt, an iridium salt or a complex salt thereof, a rhodium salt or a complex salt thereof, or an iron salt or a complex salt thereof may be present during precipitation or physical ripening of the silver halide grains in order to improve contrast and reciprocity law failure property.

The silver halide photographic emulsions of this invention may contain various compounds for preventing the formation of fog during the production of photographic materials, preserving or processing the photographic materials, or for stabilizing the photographic properties of the photographic materials. For example, there are many compounds known as antifoggants or stabilizers, such as azoles as benzothiazolium salts, nitroindazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (in particular, 1-phenyl-5-mercaptotetrazole), etc.; mercaptopyrimidines; mercaptotriazines; thioketo compounds as oxazolinethione; azaindenes as triazaindenes, tetraazaindenes (in particular, 4-hydroxy substituted (1,3,3a,7)tetraazaindene), pentaazaindenes, etc.; benzenethiosulfonic acid; benzenesulfinic acid; and benzenesulfonic acid amide. Among these stabilizers, tetraazaindenes are particularly preferred. These stabilizers are preferably added during chemial ripening, or after ripening but before coating the silver halide emulsion.

The silver halide photographic emulsions of this invention may contain an inorganic or organic hardening agent. For example, a chromium salt (chromium alum, chromium acetate, etc.), an aldehyde (formaldehyde, glyoxal, glutaraldehyde, etc.), an active vinyl compound (1,3,5-triacryloylhexahydro-S-triazine, etc.), an active halogen compound (2,4-dichloro-6-hydroxy-S-triazine, etc.), a mucohalogenic acid, etc., can be used.

Photographic couplers which can be used in the present invention include compounds capable of forming dyes upon oxidative coupling with an aromatic primary amine developing agent (for example, a phenylenediamine derivative, an aminophenol derivative, etc.) in the color development processing. For instance, for magenta couplers, there are 5-pyrazolone couplers, pyrazolobenzimidazole couplers, cyanoacetylcoumarone couplers, open chain acylacetonitrile couplers, etc.; for yellow couplers, there are acylacetoamide couplers (for example, benzoylacetanilides, pivaloylacetanilides, etc.), etc.; and for cyan couplers, there are naphthol couplers, phenol couplers, etc.

The light-sensitive material of the present invention may contain hydroquinone derivatives, aminophenol derivatives, gallic acid derivatives, ascorbic acid derivatives, etc., as color fog preventing agents.

The photographic emulsion layers and other hydrophilic colloid layers of the light-sensitive material according to the present invention may contain a wide variety of known surface active agents for various purposes such as for improving coating property, preventing static phenomenon, improving slipping property, improving emulsification and dispersion properties, preventing adhesion, as well as improving photographic characteristics (e.g., development acceleration, contrasting, sensitization, etc.).

Examples of these surface active agents are nonionic surface active agents such as saponin (steroid series), alkylene oxide derivatives (e.g., polyethylene glycol, polyethylene glycol/polypropylene glycol condensate, polyethylene glycol alkyl ether, polyethylene glycol alkylaryl ether, polyethylene glycol esters, polyethylene glycol sorbitan esters, polyalkylene glycol alkylamines, polyalkylene glycol alkylamides, polyethylene oxide addition products of silicones, etc.), glycidol derivatives (e.g., polyglyceride alkenylsuccinate, alkylphenol polyglyceride, etc.), fatty acid esters of polyhydric alcohols, alkyl esters of sugar, urethanes and ethers; anionic surface active agents containing acid groups as carboxy group, sulfo group, phospho group, sulfuric acid ester group, phosphoric acid ester group, etc., such as triterpenoidsaponin, alkylcarboxylates, alkylsulfonates, alkylbenzenesulfonates, alkylnaphthalene-sulfonates, alkylsulfuric acid esters, alkylphosphoric acid esters, N-acyl-N-alkyltaurines, sulfosuccinic acid esters, sulfoalkylpolyoxyethylene alkylphenyl ethers, polyoxyethylene alkylphosphoric acid esters, etc.; amphoteric surface active agents such as amino acids, aminoalkylsulfonic acids, aminoalkylsulfuric acid esters, aminoalkylphosphoric acid esters, alkylbetaines, amine imides, amine oxides, etc.; and cationic surface active agents such as alkylamines, aliphatic quaternary ammonium salts, aromatic quaternary ammonium salts, heterocyclic quaternary ammonium salts (e.g., pyridinium, imidazolium, etc.), phosphonium or sulfonium salts containing heterocyclic rings, and aliphatic phosphonium or sulfonium salts.

In the present invention, fluorine-containing surface active agents can also be used. For example, fluorine-containing surface active agents as described in British Pat. Nos. 1,330,356, 1,524,631, U.S. Pat. Nos. 3,666,478, 3,589,906, Japanese Pat. No. 26687/77, Japanese Patent Application (OPI) Nos. 46733/74, 32322/76 (The term "OPI" as used herein refers to a "published unexamined Japanese patent application"), etc., can be used.

Typical examples of such fluorine-containing surface active agents include N-perfluorooctylsulfonyl-N-propylglycin potassium salt, 2-(N-perfluorooctylsulfonyl-N-ethylamino)ethyl phosphate, N-[4-(perfluorononenyloxy)-benzyl]-N,N-dimethylammonium acetate, N-[3-(N',N',N'-trimethylammonio)propyl]perfluorooctylsulfonamido iodide, N-(polyoxyethylenyl)-N-propylperfluorooctyl sulfonamide $(C_8F_{17}SO_2N(C_3H_7)(CH_2CH_2O)_nH)$ wherein n is from 1 to 50, and fluorine-containing succinic acid type compounds, and so forth.

Furthermore, the photographic light-sensitive materials using a silver halide photographic emulsion according to the present invention can contain a wide variety of additives for photography, such as antistatic agents other than the above-described surface active agents (for example, ionic polymers as described, for example, in U.S. Pat. No. 3,938,999, *Research Disclosure*, Vol. 162, page 48, etc.; metal oxides as described, for example, in U.S. Pat. Nos. 3,062,700, 3,245,833 and 3,525,621, etc., colloidal silica, etc.); polymer vehicles (for example, gelatin, gelatin derivatives, graft polymers between gelatin and other polymers, proteins such as albumin, casein, etc.; cellulose derivatives such as hydroxyethyl cellulose, carboxymethyl cellulose, cellulose sulfates, etc.; sodium alginate, saccharide derivatives such as starch derivatives, etc.; and various synthetic hydrophilic polymeric materials, for example, homo- or copolymers such as polyvinyl alcohol, polyvinyl alcohol partial acetal, poly-N-vinylpyrrolidone, polystyrene sulfonic acid, polyacrylic acid, polymethacrylic acid, polyacrylamide, polyvinylimidazole, polyvinylpyrazole, etc.); polymer latexes (for example, polymers comprising, as the monomer component, individually or in combination, alkyl (meth)acrylates, alkoxyalkyl (meth)acrylates, glycidyl (meth)acrylates, (meth)acrylamides, vinyl esters (for example, vinyl acetate), acrylonitrile, olefins, styrene, etc., or combination thereof with acrylic acid, methacrylic acid, α,β-unsaturated dicarboxylic acids, hydroxyalkyl (meth)acrylates, sulfoalkyl (meth)acrylates, styrene sulfonic acid, etc.), matting agents, whitening agents, spectral sensitizing dyes, dyestuffs, etc. These additives, as well as the supports for the photographic light-sensitive materials, coating methods, development processing methods for the photographic materials, etc., may refer to the descriptions of *Research Disclosure*, Vol. 92, pages 107 to 110 (1971, Dec.).

The silver halide photographic light-sensitive materials using a photographic emulsion according to the present invention have high sensitivity as well as resulting in the formation of less fog. Also, when the photographic materials are preserved for a long period of time under high temperature and high humidity conditions, the reduction in photographic properties such as the increase of fog with the passage of time, the reduction in sensitivity, etc., is less.

The photographic light-sensitive materials to which the present invention can be applied are not restricted. For example, it can be applied to ordinary black and white light-sensitive materials, light-sensitive materials for lithography, light-sensitive materials for X-ray, color negative light-sensitive materials, color papers, color reversal light-sensitive materials, autopositive light-sensitive materials, light-sensitive materials for diffusion transfer process, and so forth.

The present invention will be explained in greater detail with reference to the following examples, but the present invention should not be construed as being limited thereto.

EXAMPLE 1

To a silver iodobromide gelatino emulsion (mean grain size of silver halide grains being 1.3 microns) containing 1.5 mol% silver iodide, 0.6 mg per mol of silver halide of chloroauric acid and 3.4 mg per mol of silver halide of sodium thiosulfate were added. The emulsion was heated for 50 minutes at 60° C. to perform ripening. To the silver halide emulsion thus obtained, 4-hydroxy-6-methyl-1,3,3a,7-tetraazaindene as a stabilizer, 5-nitrobenzotriazole as an antifogging agent and further the compound shown in Table 1 below were added and the resulting mixture was coated on a film to prepare Samples 1 to 12, respectively. Each of these samples were exposed using a sensitometer and developed for 90 seconds using a developer, RD-III (made by Fuji Photo Film Co., Ltd.) for an automatic processor, Fuji-RN (made by Fuji Photo Film Co., Ltd.). The photographic properties of the samples were measured and the results are shown in Table 1 below. In Table 1, the sensitivity of Sample 1 was taken as 100, and the other sensitivities are shown relatively.

TABLE 1

| Sample No. | Compound | Amount Added (g/mol AgX) | Sensitivity | Fog |
|---|---|---|---|---|
| 1 (Blank) | — | — | 100 | 0.03 |
| 2 (Present invention) | Compound (2) | 8.5 | 129 | 0.04 |
| 3 (Present invention) | Compound (2) | 17 | 135 | 0.03 |
| 4 (Present invention) | Compound (3) | 8.5 | 115 | 0.04 |
| 5 (Present invention) | Compound (15) | 8.5 | 117 | 0.02 |
| 6 (Present invention) | Compound (15) | 17 | 122 | 0.01 |
| 7 (Present invention) | Compound (7) | 8.5 | 110 | 0.03 |
| 8 (Present invention) | Compound (9) | 8.5 | 115 | 0.04 |
| 9 | | | | |

TABLE 1-continued

| Sample No. | Compound | Amount Added (g/mol AgX) | Sensitivity | Fog |
|---|---|---|---|---|
| (Present invention) 10 | Compound (10) | 8.5 | 115 | 0.04 |
| (Comparison) 11 | Sodium p-Styrene Sulfonic Acid | 17 | 101 | 0.04 |
| (Comparison) 12 | Acrylic Acid | 17 | 90 | 0.03 |
| (Comparison) | Dimethyl Dodecyl Ammonio Acetate Betaine* | 8.5 | 100 | 0.04 |

*$C_{12}H_{25}\overset{\oplus}{N}(CH_3)_2$ (betaine compound having surface activity)
 |
 $CH_2COO^{\ominus}$ It is apparent from the results shown in Table 1 above that Samples 2 to 9 using the compounds according to the present invention has high sensitivity without an accompanying increase in the formation of fog. On the other hand, the compounds used for comparison did not show such effects.

EXAMPLE 2

An aqueous gelatin solution containing potassium iodide and potassium bromide was maintained at 70° C. with stirring, and thereto an aqueous solution of potassium bromide and an aqueous solution of silver nitrate were simultaneously added to prepare a silver iodobromide emulsion (containing 5 mol% silver iodide) having 0.8 micron mean grain size.

The silver halide emulsion was cooled, set, and washed with water to remove the unnecessary salts in a conventional manner. The pH value and pAg value of the emulsion were adjusted to 6.5 and 8.9, respectively. The emulsion was heated at 60° C., to which sodium thiosulfate and potassium chloroaurate were added and subjected to chemical ripening for 60 minutes.

After adding the sensitizing dye, the stabilizer, the color coupler, the gelatin hardener, the coating aid described below, and the compound described in Table 2 below, the silver halide emulsion was coated on a cellulose acetate film support and dried.

Sensitizing Dye: 5,5'-dichloro-3,3'-di($\gamma$-sulfopropyl)-9-ethyloxacarbocyanine sodium salt
Stabilizer: 4-hydroxy-6-methyl-1,3,3a,7-tetraazaindene
Coupler: 1-(2,4,6-trichlorophenyl)-3-[3-(2,4-di-tertamylphenoxy)acetamido]benzamido-5-pyrazolone
Gelatin Hardener: 2,4-dichloro-6-hydroxy-s-triazine
Coating Aid: sodium dodecylbenzenesulfonate Each of these samples was exposed (1/100 second) through an optical wedge and subjected to the color development processing described below. The photographic properties of the samples were measured and the results were shown in Table 2 below.

In Table 2, the photographic sensitivity is shown by a reciprocal of the exposure amount required for obtaining an optical density of fog value +0.20 and the sensitivity of Sample 13 is taken as 100 and the other sensitivities are shown relatively.

| Processing Step | Temperature (°C.) | Time |
|---|---|---|
| 1. Color development | 38 | 3 min 15 sec |
| 2. Bleach | " | 6 min 30 sec |
| 3. Wash | " | 3 min 15 sec |
| 4. Fix | " | 6 min 30 sec |
| 5. Wash | " | 3 min 15 sec |
| 6. Stabilization | " | 3 min 15 sec |

The compositions of the processing solutions used in the above processing were as follows:

| Color Developer Solution: | | |
|---|---|---|
| Sodium Nitrotriacetate | 1.0 | g |
| Sodium Sulfite | 4.0 | g |
| Sodium Carbonate | 30.0 | g |
| Potassium Bromide | 1.4 | g |
| Hydroxylamino Sulfate | 2.4 | g |
| 4-(N-Ethyl-N-$\beta$-hydroxyethylamino)-2-methylaniline Sulfate | 4.5 | g |
| Water to make | 1 | l |
| Bleaching Solution: | | |
| Ammonium Bromide | 160.0 | g |
| Aqueous Ammonia (28%) | 25.0 | ml |
| Ethylenediaminetetraacetic Acid Sodium Iron Salt | 130 | g |
| Glacial Acetic Acid | 14 | ml |
| Water to make | 1 | l |
| Fixing Solution: | | |
| Sodium Tetrapolyphosphate | 2.0 | g |
| Sodium Sulfite | 4.0 | g |
| Ammonium Thiosulfate (70%) | 175.0 | ml |
| Sodium Hydrogensulfite | 4.6 | g |
| Water to make | 1 | l |
| Stabilization Solution: | | |
| Formalin | 8.0 | ml |
| Water to make | 1 | l |

TABLE 2

| Sample No. | Compound | Amount Added (g/mol AgX) | Sensitivity | Fog |
|---|---|---|---|---|
| 13 (Blank) | — | — | 100 | 0.10 |
| 14 (Present invention) | Compound (2) | 8.5 | 120 | 0.10 |
| 15 (Present invention) | Compound (2) | 17.0 | 140 | 0.11 |
| 16 (Present invention) | Compound (15) | 8.5 | 125 | 0.10 |
| 17 (Present invention) | Compound (15) | 17.0 | 130 | 0.11 |
| 18 (Comparison) | Acrylic Acid | 17.0 | 95 | 0.10 |
| 19 (Comparison) | Sodium p-Styrene Sulfonic Acid | 17.0 | 100 | 0.10 |

It is apparent from the results shown in Table 2 above that in Samples (14) to (17) according to the present invention the sensitivity is increased without an accompanying increase in the formation of fog.

EXAMPLE 3

A silver halide emulsion containing 80 mol% silver chloride, 19.5 mol% silver bromide and 0.5 mol% silver iodide was subjected to gold sensitization and sulfur sensitization. The mean grain size of the silver halide grains was 0.35 micron.

Then, 625 g each of the silver halide emulsion was placed in each of 10 pots and after adding thereto the compound as shown in Table 3 below and further an appropriate amount of 3-carboxymethyl-5-[2-(3-ethyl-thiazolinylidene)ethylidene]rhodanine (optical sensitizer), 4-hydroxy-1,3,3a,7-tetraazaindene (stabilizer), a polyoxyethylene compound described below (dot quality improving agent), mucochloric acid (hardening agent) and the polymer latex described in Production Formulation 3 of Japanese Pat. No. 5331/70, and resultant mixture was coated on a polyethylene terephthalate film base to provide each photographic light-sensitive material.

Each of these light-sensitive materials was brought into close contact with a positive gray contact screen and exposed to a white tungsten light for 10 seconds through a step wedge having a step differential of 0.1. After exposure, the samples were developed for 100 seconds at 27° C. using the developer solution having the composition shown below, and fixed and washed with water in a conventional manner.

After processing, the dot quality was evaluated in four grades of A: excellent, B: acceptable in practical use, C: poor, and D: very poor, by observing dots in 50% blackened areas with a microscope of 100 magnifications.

Also, the sensitivity was evaluated by exposing, processing and sensitometry in the same manner as described above but without using a contact screen. The sensitivity was compared as the reciprocal of the exposure amount for obtaining the optical density of 1.50 and shown relatively by defining the sensitivity of Sample 21 to be 100.

| Developer Solution: | |
| --- | --- |
| Hydroquinone | 15 g |
| Addition Product of Formaldehyde and Sodium Bisulfite | 50 g |
| Potassium Carbonate | 30 g |
| Sodium Sulfite | 2.5 g |
| Potassium Bromide | 2.0 g |
| Boric Acid | 5.0 g |
| Sodium Hydroxide | 3.0 g |
| Triethylene Glycol | 40 g |
| Ethylenediaminetetraacetic Acid . 2-Sodium Salt | 1.0 g |
| Diethanolamine | 15 g |
| Water to make | 1,000 ml |
| Polyoxyethylene Compound $HO(CH_2CH_2O)_a(CHCH_2O)_b(CH_2CH_2O)_cH$ | |

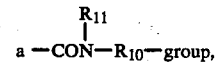
b = 8, a + c = 50

TABLE 3

| Sample No. | Compound | Amount Added (g) | Sensitivity | Dot Quality |
| --- | --- | --- | --- | --- |
| 21 (Blank) | — | — | 100 | C |
| 22 (Present invention) | Compound (2) | 6.0 | 115 | B |
| 23 (Present invention) | Compound (2) | 12.0 | 124 | A |
| 24 (Present invention) | Compound (2) | 24.0 | 125 | A |
| 25 (Present invention) | Compound (3) | 6.0 | 117 | B |
| 26 (Present invention) | Compound (3) | 12.0 | 125 | A |

TABLE 3-continued

| Sample No. | Compound | Amount Added (g) | Sensitivity | Dot Quality |
| --- | --- | --- | --- | --- |
| 27 (Present invention) | Compound (3) | 24.0 | 125 | A |
| 28 (Comparison) | Sodium p-Styrene Sulfonic Acid | 6.0 | 100 | C |
| 29 (Comparison) | Sodium p-Styrene Sulfonic Acid | 12.0 | 100 | C |
| 30 (Comparison) | Sodium p-Styrene Sulfonic Acid | 24.0 | 100 | C |

It is apparent from the results shown in Table 3 above that Samples (22) to (27) according to the present invention provide a high sensitivity and an excellent dot quality.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising a support having coated therein at least one silver halide emulsion layer, said photographic light-sensitive material containing a sensitizing amount of a compound represented by formula (I)

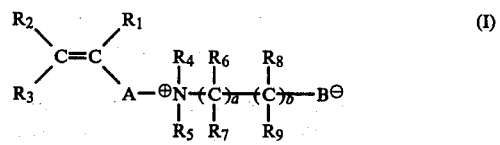

wherein $R_1$, $R_2$, and $R_3$ each represents hydrogen, an alkyl group, a carboxy group, or a substituted alkyl group; $R_4$ and $R_5$ each represents hydrogen, an alkyl group, a substituted alkyl group, or an aralkyl group, or $R_4$ and $R_5$ together represent an atomic group forming a heterocyclic ring or an atomic group forming a heterocyclic ring together with A; $R_6$, $R_7$, $R_8$, and $R_9$ each represents hydrogen, an alkyl group or a substituted alkyl group; A represents a divalent connecting group which is an ether group, an alkylene group, a substituted alkylene group, an arylene group, a substituted arylene group, an aralkylene group, a substituted aralkylene group, a —COOR$_{10}$-group, a —OCO—R$_{10}$-group, $$a\ -CON-R_{10}-group,$$
$$\phantom{a\ -CO}|\phantom{N-R_{10}-group,}$$
$$\phantom{a\ -CON-}R_{11}$$

or an atomic group forming a heterocyclic ring together with $R_4$ and $R_5$;

wherein $R_{10}$ represents a divalent group selected from an alkylene group, an arylene group, and an aralkylene group, or an atomic group forming a heterocyclic ring together with $R_4$ or $R_5$;

and wherein $R_{11}$ represents hydrogen, an alkyl group, or an atomic group forming a heterocyclic ring together with $R_4$ and $R_{10}$, or $R_5$ and $R_{10}$; a and b can each represents 0 or a positive integer, provided that a and b are not both 0; and B represents —COO or —SO$_3$.

2. A silver halide photographic light-sensitive material as in claim 1, wherein said alkyl groups represented by $R_1$ through $R_9$ each contains from 1 to 6 carbon atoms.

3. A silver halide photographic light-sensitive material as in claim 1, wherein said substituted alkyl groups represented by $R_1$ through $R_9$ each is an alkyl group containing from 1 to 6 carbon atoms, and is substituted with a member selected from a hydroxy group, a halogen atom, and a nitro group.

4. A silver halide photographic light-sensitive material as in claim 1, wherein said aralkyl group represented by $R_4$ or $R_5$ has from 7 to 11 carbon atoms.

5. A silver halide photographic light-sensitive material as in claim 1, wherein said heterocyclic ring formed from $R_4$ and $R_5$ is a morpholine ring.

6. A silver halide photographic light-sensitive material as in claim 1, wherein said heterocyclic ring formed from $R_4$, $R_5$, and A is a pyridine ring or an imidazole ring.

7. A silver halide photographic light-sensitive material as in claim 1, wherein $R_1$, $R_2$, and $R_3$ each represents hydrogen, a lower alkyl group, or a carboxy group; $R_4$ and $R_5$ each represents a lower alkyl group or an atomic group forming a pyridine ring or an imidazole ring, or $R_4$ and $R_5$ together represent an atomic group forming a morpholine ring; $R_6$, $R_7$, $R_8$, and $R_9$ each represents hydrogen or a methyl group; A represents

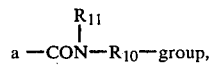

a —COOR$_{10}$-group, or an atomic group forming a pyridine ring or an imidazole ring together with $R_4$ and $R_5$; a and b each represents 0 or a positive integer from 1 to 4, provided that a and b are not both 0; and B represents —COO or —SO$_3$;

wherein $R_{10}$ represents a divalent group selected from an alkylene group, an arylene group, and an aralkylene group, or an atomic group forming a heterocyclic ring together with $R_4$ or $R_5$;

and wherein $R_{11}$ represents hydrogen, an alkyl group, or an atomic group forming a heterocyclic ring together with $R_4$ and $R_{10}$, or $R_5$ and $R_{10}$.

8. A silver halide photographic light-sensitive material as in claim 7, wherein $R_1$, $R_2$, and $R_3$ each represents hydrogen, a methyl group, an ethyl group, or a carboxy group; $R_4$ and $R_5$ each represents a methyl group, an ethyl group, or an atomic group forming a pyridine ring, an imidazole ring, or $R_4$ and $R_5$ together represent an atomic group forming a morpholine ring; $R_6$, $R_7$, $R_8$, and $R_9$ each represents hydrogen or a methyl group; A represents

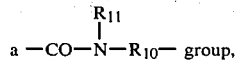

a —COO—R$_{10}$-group, or an atomic group forming a pyridine ring or an imidazole ring together with $R_4$ and $R_5$; a and b each represents 0 or a positive integer from 1 to 4, provided that a and b are not both 0; and B represents —COO or —SO$_3$;

wherein $R_{10}$ represents a divalent group selected from an alkylene group, an arylene group, and an aralkylene group, or an atomic group forming a heterocyclic ring together with $R_4$ or $R_5$;

and wherein $R_{11}$ represents hydrogen, an alkyl group, or an atomic group forming a heterocyclic ring together with $R_4$ and $R_{10}$, or $R_5$ and $R_{10}$.

9. A silver halide photographic light-sensitive material as in claim 7, wherein $R_1$, $R_2$, and $R_3$ each represents hydrogen or a methyl group; $R_4$ and $R_5$ each represents a methyl group or an ethyl group; $R_6$, $R_7$, $R_8$, and $R_9$ each represents hydrogen or a methyl group; A represents

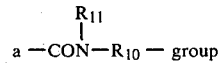

or a —COOR$_{10}$-group; a and b each represents 0, 1, or 2, provided that a and b are not both 0; and B represents —COO or —SO$_3$;

wherein $R_{10}$ represents a divalent group selected from an alkylene group, an arylene group, and an aralkylene group, or an atomic group forming a heterocyclic ring together with $R_4$ or $R_5$;

and wherein $R_{11}$ represents hydrogen, an alkyl group, or an atomic group forming a heterocyclic ring together with $R_4$ and $R_{10}$, or $R_5$ and $R_{10}$.

10. A silver halide photographic light-sensitive material as in claim 9, wherein $R_{10}$ represents an alkylene group or an aralkylene group and $R_{11}$ represents hydrogen or a methyl group.

11. A silver halide photographic light-sensitive material as in claim 9, wherein A represents

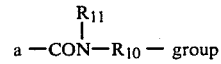

and $R_{11}$ represents an atomic group forming a piperazine ring together with $R_4$ and $R_{10}$, or $R_5$ and $R_{10}$.

12. A silver halide photographic light-sensitive material as in claim 1, wherein said compound is present in a silver halide emulsion layer or a layer adjacent thereto.

13. A silver halide photographic light-sensitive material as in claim 1, wherein said compound is present in a silver halide emulsion layer.

14. A silver halide photographic light-sensitive material as in claim 1, 2, 3, 4, 5, 6, 7, 8, 9, 10, 11, 12, or 13, wherein the amount of said compound is from about 0.001 mol to 1 mol per mol of silver halide in the silver halide emulsion layer.

15. A silver halide photographic light-sensitive material as in claim 1, 2, 3, 4, 5, 6, 7, 8, 9, 10, 11, 12, or 13, wherein the amount of said compound is from 0.01 mol to 0.5 mol per mol of silver halide in the silver halide emulsion layer.

16. A silver halide photographic light-sensitive material as in claim 13 prepared by adding said compound to the silver halide emulsion during or after chemical ripening thereof, but before coating of said emulsion.

17. A silver halide photographic light-sensitive material as in claim 16, wherein the pAg of the silver halide emulsion during chemical ripening is from about 8.0 to 11.0.

18. A silver halide photographic light-sensitive material as in claim 1, wherein said silver halide emulsion is chemically sensitized.

* * * * *